United States Patent [19]

Handjani et al.

[11] Patent Number: 5,204,111
[45] Date of Patent: Apr. 20, 1993

[54] PROCESS FOR THE PREPARATION OF ALGINATE CAPSULES, APPARATUS FOR PRODUCING SAID CAPSULES AND COSMETIC COMPOSITIONS CONTAINING SAID CAPSULES

[75] Inventors: Rose-Marie Handjani, Paris; Myriam Kauffmann, Lyons; Frédéric Huguenin, Paris, all of France

[73] Assignee: L'Oreal, Paris, France

[21] Appl. No.: 826,610

[22] Filed: Jan. 28, 1992

Related U.S. Application Data

[62] Division of Ser. No. 505,687, Apr. 9, 1990, Pat. No. 5,139,783.

[30] Foreign Application Priority Data

Apr. 7, 1989 [FR] France ................ 89 04598

[51] Int. Cl.$^5$ .................. A61K 7/00; A61K 9/48; A61K 31/725
[52] U.S. Cl. .................. 424/451; 424/401; 424/195.1; 424/489; 424/499; 428/402; 514/779; 514/844; 514/962; 536/3
[58] Field of Search ............... 424/451, 401, 497, 401, 424/489

[56] References Cited

U.S. PATENT DOCUMENTS

| | | | |
|---|---|---|---|
| 4,352,883 | 10/1982 | Lim | 424/496 |
| 4,692,284 | 9/1987 | Braden | 424/461 |
| 4,701,326 | 10/1987 | Nelsen et al. | 424/452 |
| 4,749,620 | 6/1988 | Rha et al. | 424/455 |
| 4,765,984 | 8/1988 | Vellekoop et al. | 424/441 |
| 4,806,357 | 2/1989 | Garrett et al. | 427/4 |
| 4,923,645 | 5/1990 | Tsang et al. | 424/493 |

FOREIGN PATENT DOCUMENTS

62169485  5/1989  Japan.
1236885   6/1971  United Kingdom.

OTHER PUBLICATIONS

A. Kondo: "Microcapsule Processing and Technology", 1979 pp. 65–66, M. Dekker Inc., New York.

Primary Examiner—Thurman K. Page
Assistant Examiner—James M. Spear
Attorney, Agent, or Firm—Cushman, Darby & Cushman

[57] ABSTRACT

A process for producing alginate capsules comprises slowly introducing an aqueous alginate solution into crosslinking solution of a polyvalent metal salt. The aqueous alginate solution has mannuronic units (M) and guluronic units (G) in a molar ratio between 0.4 and 1.9 and preferably an amount of (G) blocks greater than 50%. Preferably, the alginate is a sodium alginate having a viscosity, in a 0.5% solution in water at 25° C., lower than 20 mPa.s measured with a TV Contraves viscosimeter having a No. 1 measurement body in the presence of a calcium chelate. The alginate concentration is between 0.2 and 2 weight percent. The polyvalent metal salt concentration in solution is from $3.4 \times 10^{-3}$ to $6.8 \times 10^{-2}$M. The alginate capsules are employed in cosmetic compositions.

1 Claim, 3 Drawing Sheets

PROCESS FOR THE PREPARATION OF ALGINATE CAPSULES, APPARATUS FOR PRODUCING SAID CAPSULES AND COSMETIC COMPOSITIONS CONTAINING SAID CAPSULES

This is a division of application Ser. No. 07/505,687, filed Apr. 9, 1990, now U.S. Pat. No. 5,139,783.

The present invention relates to a process for preparing alginate capsules that are particularly adapted for cosmetic uses. The present invention is also concerned with the apparatus employed to implement the process as well as to a cosmetic composition containing the capsules prepared by the said process.

Alginates are known products; they are constituted by polysaccharide chains obtained by linking two types of monomers, guluronic acid (G) and mannuronic acid (M), which organize into blocks G, blocks (M) and blocks with alternating G-M monomers. Gelification is effected by bridging these polysaccharide chains with polyvalent ions. This bridging is effected preferably between the G blocks.

The production of alginate capsules by gelification of aqueous solutions of soluble alginate salts, such as salts of potassium, magnesium, ammonium and preferably sodium, or aqueous solutions of their derivatives, such as their partial esters, by means of certain polyvalent metallic cations, in particular, calcium, is known. To prepare alginate capsules, an alginate solution is let fall dropwise, using a nozzle, into a solution of a polyvalent metal salt. The resulting capsules are then separated from the crosslinking medium.

In order that the resulting capsules can be employed in cosmetics, it is necessary that they have, at the same time, the following two antagonistic properties: they are easily crushed on the skin, without leaving a residue, under the action of a slight massage, and then have sufficient rigidity so that their structure is not modified in the course of storage or, their incorporation into a cosmetic composition.

The applicants have found, in accordance with the present invention, that by adjusting, in a precise manner, the conditions for producing the alginate capsules, in particular the crosslinking kinetic conditions during the course of production, alginate capsules having the requisite properties for cosmetic usage can be obtained.

Figure 1:
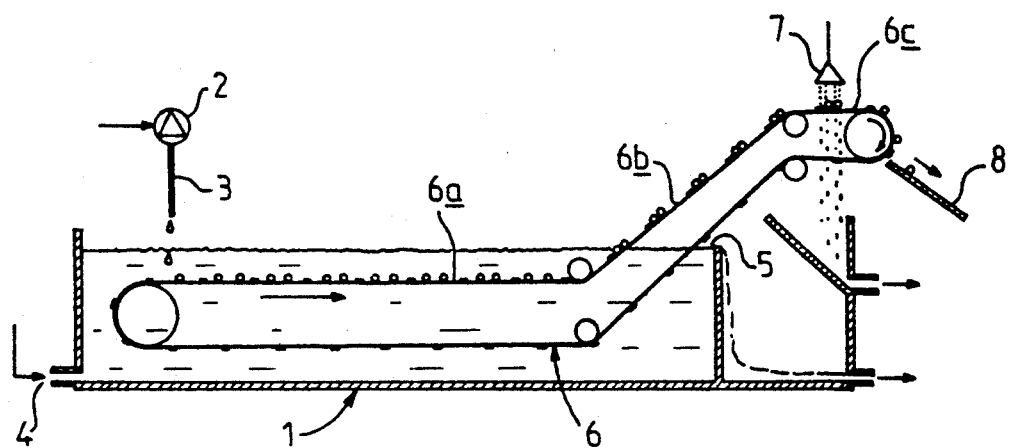
FIG. 1 schematically shows an apparatus of the type for performing the invention.

The present invention concerns a process for producing alginate capsules by slowly introducing an aqueous solution of at least one alginate into an aqueous solution of at least one polyvalent metal salt selected from iron, silver, strontium, aluminum, manganese, selenium and, in particular, a calcium, copper or zinc salt, using at least one nozzle, then extracting or removing the alginate capsules, formed by gelification, so as to separate them from the aqueous solution of polyvalent metal salt and finally, optionally washing and drying said capsules, where in said process:

(a) at least one alginate having mannuronic units (M) and guluronic units (G) in an M/G molar ratio between 0.1 and 1.9 and, preferably, an amount of (G) blocks greater than 50% is employed. The alginate is, preferably, a sodium alginate having a viscosity, in a 0.5 weight percent aqueous solution at 25.C, lower than 20 mPa.s measured with a TV Contraves viscosimeter having a No. 1 measurement body, in the presence of a calcium chelating agent;

(b) the alginate weight concentration of the aqueous solution introduced through the nozzle is between 0.2 and 2%, preferably between 0.3 and 1%;

(c) the polyvalent metallic cation molar concentration of the crosslinking aqueous solution of polyvalent metal salt is $3.4 \times 10^{-3}$M to $6.8 \times 10^{-2}$M, and preferably, between $8.8 \times 10^{-3}$M to $3.4 \times 10^{-2}$M;

(d) the surface tension of the aqueous solution of polyvalent metal salt is reduced to a value lower than 70 dynes/cm, preferably near 40 dynes/cm, by the addition of a surfactant; and (e) the contact time between the droplets of alginate solution and the aqueous solution of polyvalent metal salt is between 10 seconds and 20 minutes, preferably between 30 seconds and 10 minutes.

Under these conditions, alginate capsules are obtained which are spherical, spheroidal, oval or in the form of drops or grains of rice, having a texture adapted for cosmetic usage; when they are spheroidal, they can have a diameter between 100 μm and 1 cm and preferably between 500 μm and 0.8 cm.

In accordance with the present invention the aqueous alginate solution can contain at least one water soluble or dispersible cosmetic additive or active agent, optionally containing liposoluble additives or active agents, or mineral or organic solids which remain in dispersion or in suspension in the alginic matrix. Representative useful active agents include biological compounds, vegetable or animal extracts, colored or colorless pigments, mineral fillers, sunscreen agents, soluble or insoluble polymers, floral water, essential oils, perfume, substances for buccal hygiene and dental care, liquid cholesterol type crystals, vesicular dispersions, polymeric or lipid microspheres or microcapsules, nanoparticles or nanocapsules. The active agents currently employed for buccal hygiene or for dental care can also be introduced into the aqueous alginate solution or in the external phase of a composition containing the alginate capsules. These active agents are for example:

antiseptic, anti-inflammatory, decongestion or sweetening agents (choline salicylate, vegetable extracts, glycerrhetinic acid), agents for adsorbing bad odors or molecules originating from food debris (cycodextrines, zinc ricinoleate), polishing agents (mineral powders), and substances capable of acting on the mineral portion of the tooth (strontium salts).

The aqueous alginate solution can also contain a small amount of crosslinking ions which modify its rheologic properties.

The solution of polyvalent metal salt employed is, preferably, a solution of calcium chloride, gluconate or lactate or a solution of copper or zinc acetate, sulfate, chloride or gluconate. The volume of the crosslinking solution must, in general, be sufficient so that it is not exhausted of the polyvalent metal and only reduced in strength in negligible amounts during the course of forming the capsules. Moreover, the solution must not be agitated by turbulences, which cause distortion of the capsules during their formulation.

Additionally, the density of the alginate solution must, preferably, be at least slightly higher than that of the solution of polyvalent cations, so that the falling drops are entrained toward the bottom.

In accordance with the invention, a surfactant is added to the solution of polyvalent metal salts. This surfactant can be, for example, the product sold under the trade name "TWEEN 20" by ICI Americas at a weight concentration of 0.001%.

In accordance with the present invention, one or more nozzles can be employed for introducing the aqueous alginate solution into the solution of polyvalent metal salts. The diameter of the resulting capsules depends on the dimension of the nozzles employed. For example, using a nozzle having a 0.6 millimeter diameter, spheres having a diameter of 1.5 to 2.5 millimeters are formed. Using a nozzle having a 1.5 mm diameter, spheres having a diameter of 3 to 6 mm are formed.

The alginate solution can be delivered from above the solution of polyvalent metal salts. The height of the nozzles above the surface of the crosslinking solution must then be, preferably, just sufficient so that the droplets are formed and separate from the nozzle under the effect of their own weight, or by forced shearing. If the height is too great, the droplets are deformed on their arrival in the crosslinking solution and lose their spherical form.

The alginate solution can also be injected under the surface of the crosslinking solution. In this situation, if movement is imparted to the nozzle, particles of various forms can be obtained. For example, a linear movement forms elongated capsules.

The process in accordance with the present invention develops in the following manner: the alginate solution also containing the optional active agents in solution or suspension, drip dropwise into the crosslinking solution using one or more nozzles. The drops are thus gelified and form capsules. After a precisely timed residence therein the capsules are extracted from the crosslinking medium, by, for example, screening or draining. Optionally, the excess crosslinking ions are removed by rinsing with water, preferably demineralized water. The free water at the surface of the capsules is then optionally removed by drying or draining. The capsules, after rinsing and drying, can be coated with a layer of a more or less adhesive polymer, in solution or suspension. This coating is obtained, for example, by soaking the capsules in a solution or a suspension of an adhesive acrylic polymer, such as those sold by Monsanto under the commercial names: "GELVA multipolymer emulsion 2397" and "GELVA multipolymer emulsion 3011".

The present invention also relates to a cosmetic composition containing alginate capsules, prepared by the process described above, in a cosmetically acceptable external phase. In this cosmetic composition, the external phase can be a gel, an emulsion, a solution, an oil or an oily cosmetically acceptable excipient, more or less transparent or translucent. The external phase can also include any type of additive or active agent in the cosmetic sense.

The present invention also relates to an apparatus for performing the method according to the invention, including a storage reservoir for the alginate solution, at least one nozzle for delivering said alginate solution, a pump drawing the alginate solution from the storage reservoir and supplying the nozzle or nozzles, an elongated tank supplied continuously at one of its ends with an aqueous solution of salt(s) of the crosslinking cation and including at its other end a device for drawing off said crosslinking solution, for example via overflow, and optionally a system for regenerating and recycling said solution, the alginate solution dripping from the nozzle or nozzles into the crosslinking solution at the end of the tank corresponding to the supply of polyvalent metal salt(s) and a transport device disposed longitudinally in the tank and enabling transportation of the alginate capsules being formed from one end of the tank to the other. According to the present invention, the transport device may be an endless screw; however, it preferably comprises an endless belt driven by a motor. The endless belt is preferably formed of a frame or a perforated flexible material, the mesh of which is smaller than the diameter of the drops dropping from the nozzle. The belt may be of polyamide or other polymer or stainless steel or another metal; it preferably includes transverse projections that prevent the capsules being formed from sliding backward.

In the drawing, FIG. 1 schematically shows an apparatus of this type that is usable in industry, the drawing being solely illustrative and not limiting.

Turning to the drawing, it is seen that the aqueous crosslinking solution is contained in a tank 1; the alginate solution is supplied by way of a pump 2 into the nozzles 3 and drips into the solution contained in the tank 1. The tank 1 is supplied with crosslinking solution by a conduit 4, at one of its ends and in the vicinity of its bottom; this solution is evacuated by an overflow 5 at the other end. The tank 1 contains an endless belt 6, which comprises a frame, for example of polyamide of a type known by the trademark "nylon", having meshes smaller than or equal to 1 mm in size; this belt 6 includes transverse projections; it is disposed longitudinally in the tank 1 and is actuated by a motor (not shown). The upper portion of the belt 6 passes in the vicinity of the nozzles 3. Its lower portion serves as a return. The upper zone includes a horizontal immersed portion 6a, followed by an inclined ascending portion 6b, which in turn is extended by a horizontal portion 6c; the inclined portion 6b allows the belt to exit from the tank 1. The speed of the endless belt 6 is adjustable so that the time of contact between the alginate capsules and the crosslinking solution has a precise value of between 10 seconds and 20 minutes. At the outlet of the tank 1, the endless belt drives the formed alginate capsules outside the bath. The use of an endless belt comprising a meshed frame makes it possible to drain the capsules; the transverse projections prevent the capsules from falling backward, rolling along the inclined portion 6b. The presence of the transverse projections hence makes it possible to increase the slope of the conveyor at the outlet of the aqueous solution of polyvalent metal salt(s), and consequently enables a reduction in the size of the entire installation and a shortening of the drainage time during which the reaction is poorly controlled. On the horizontal portion 6c of the endless belt, the alginate capsules are sprinkled with demineralized water by a sprinkler head 7, to eliminate excess traces of polyvalent metal salt(s).

Optionally, the capsules may be subsequently treated by a jet of air (not shown) that dries their surface. The capsules, ready for packaging, are collected at the outlet 8 of the endless belt.

The purely illustrative, non-limiting examples given below will enable better comprehension of the invention.

EXAMPLE 1

3 g of an aqueous sodium alginate solution are made to drip dropwise into an aqueous crosslinking solution obtained by dissolving calcium chloride, $CaCl_2.2H_2O$. The alginate solution is delivered by a nozzle having a diameter of 1.3 mm whose end is 15 mm above the level of the crosslinking solution. Spheres having a diameter of about 4 mm are obtained. The formed capsules are left in contact with the crosslinking solution for a determined period of time. The capsules are then removed by screening, rinsed, weighed and placed on a weighed ashless filter. The filter and the spheres are dehydrated and weighed, thereby establishing the weight of the dry residue. The $Ca^{++}$ ions of this dry residue are dosed by absorption spectrophotometry and the $Na^+$ ions by emission spectrophotometry. Curves are prepared which give, as a function of the contact time, the percentage of fixed $Ca^{++}$ and the percentage of $Na^+$ contained in the alginate capsules. In effect, the curve of variation of the percentage of $Na^+$ is a verification of good development of the sodium/calcium exchange in the alginates.

There can sensorially be estimated from the contact time variables, the resistance of the crushing of the resulting capsules. A contact time, $t_c$, and a percentage in calcium ions, $P_c$, are determined from which the optimum consistency of the capsules is obtained.

The tests have been made with alginates sold by Kelco-France under the trade name "Manugel GHB" having a viscosity of about 8 mPa.s in a 0.5% solution measured at 25° C. with a TV Contraves viscosimeter having a No. 1 measurement body, in the presence of a calcium chelating agent and with alginates sold by Sigma under the trade name "ALGINIC ACID SODIUM SALT TYPE VI moyenne viscosite (MV)" having a viscosity of about 17 mPa.s in a 0.5% solution at 25° C. measured with a TV Contraves viscosimeter having a No. 1 measurement body in the presence of a calcium chelating agent. For these alginates, the curves given in FIGS. 2 to 5 are obtained wherein the contact time T, in seconds, is given as the abscissa and the percentages in weight, P, of the $Ca^{++}$ and $Na^+$ ions with respect to the dry alginate weights are given as the ordinate.

Figure 2:
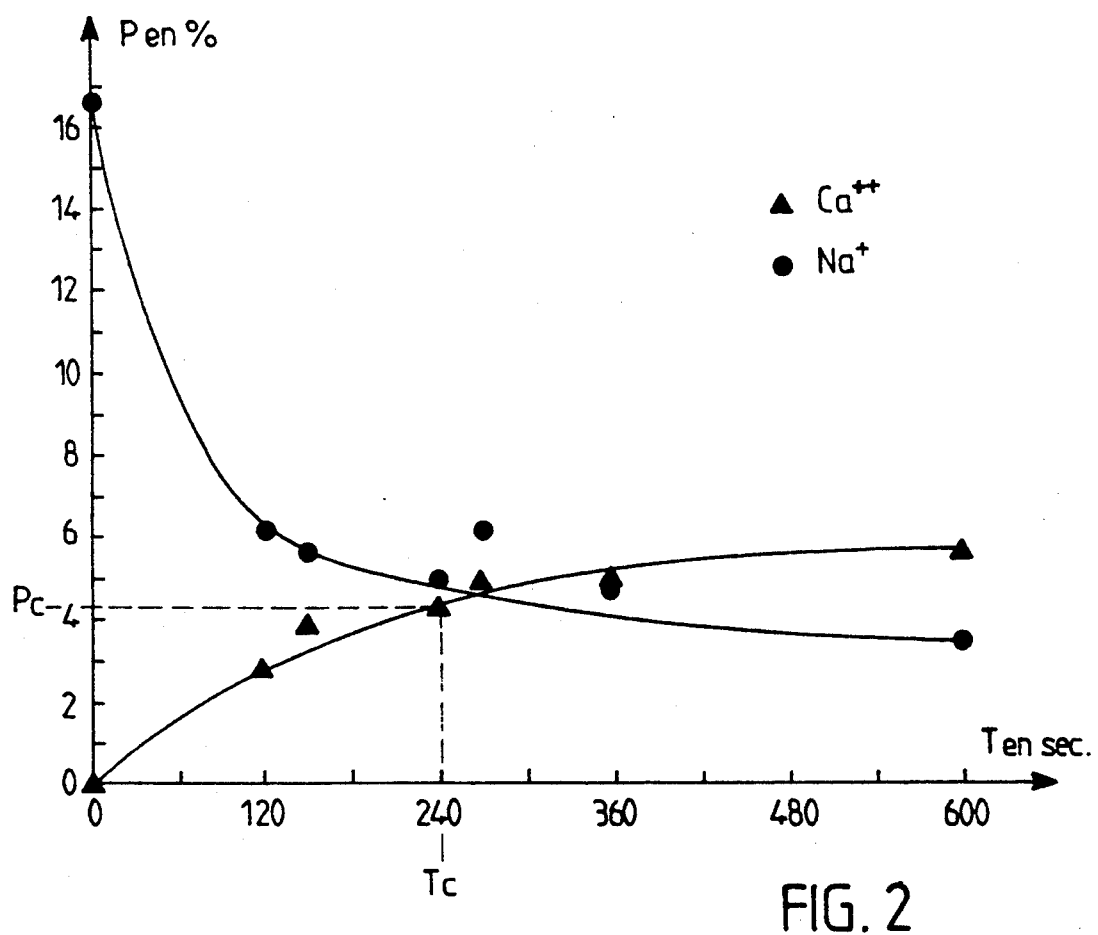
FIGS. 2 to 4 concern spheres having a diameter of 4 to 4.5 mm (nozzle having a diameter of 1.8 mm).
Figure 3:
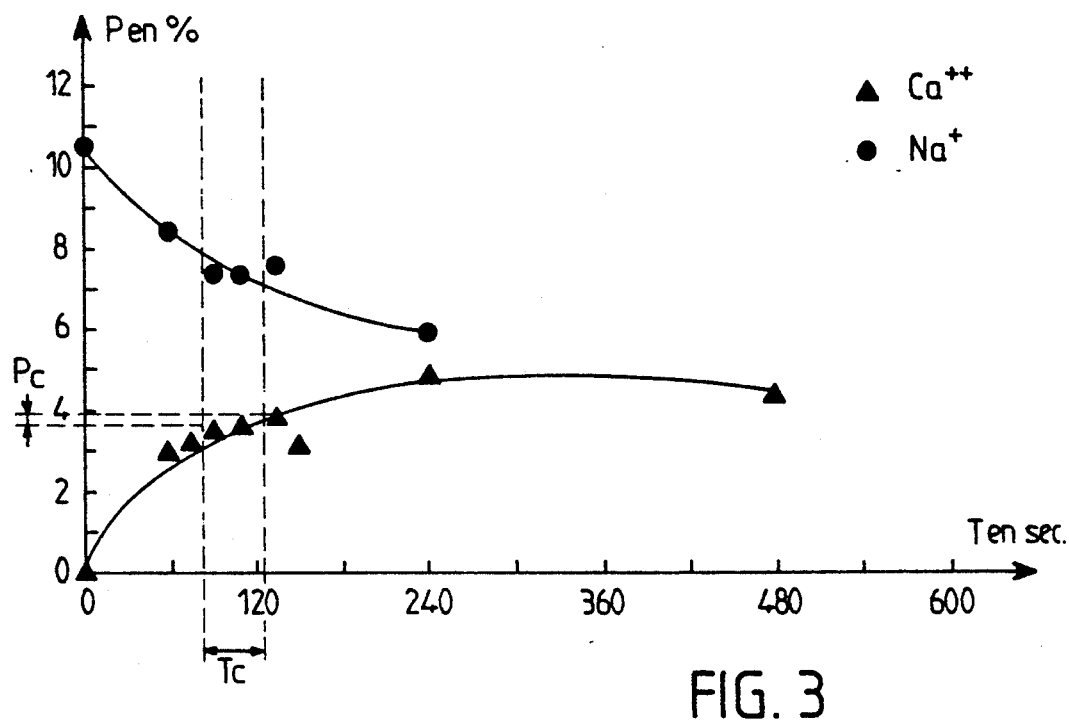
Figure 4:
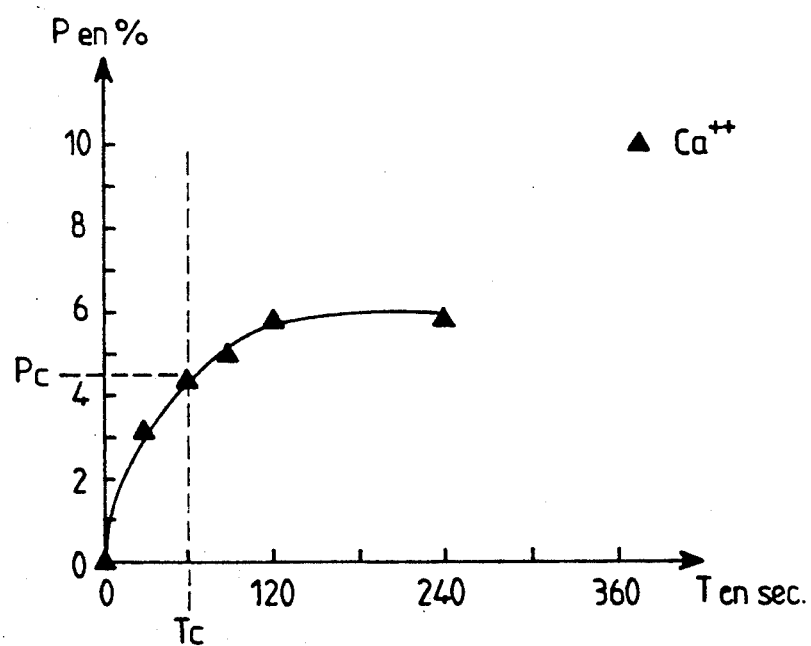
Figure 5:
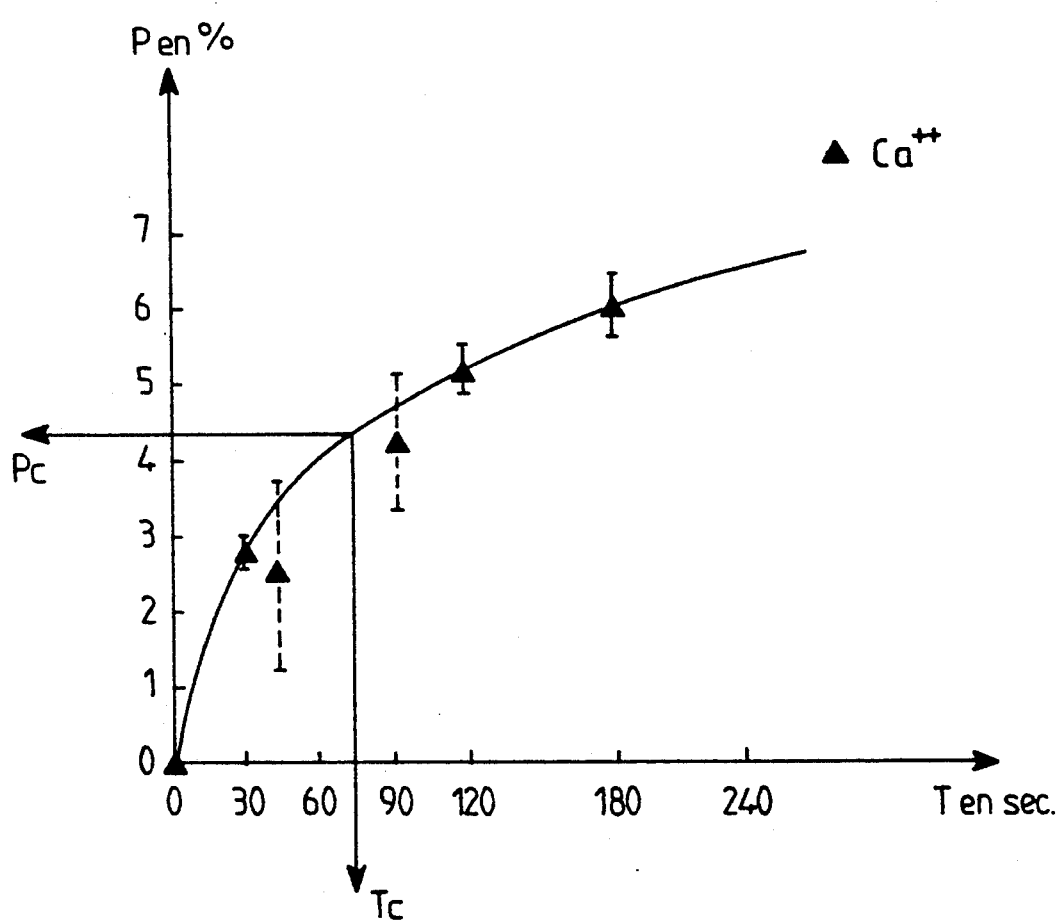
FIG. 5 concerns spheres having a diameter of 2 to 2.5 mm (nozzle having a diameter of 0.9 mm). For these alginates, the curves given in FIGS. 2 to 5 are obtained wherein the contact time T, in seconds, is given as the abscissa and the percentages in weight, P of the Ca++ and Na+ ions with respect to the dry alginate weights are given as the ordinate.

FIGS. 2 to 4 concern spheres having a diameter of 4 to 4.5 mm (nozzle having a diameter of 1.8 mm). FIG. 5 concerns spheres having a diameter of 2 to 2.5 mm (nozzle having a diameter of 0.9 mm).

On these curves it can be seen that when the Contact time between the alginate solution and the calcium chloride solution increases, it produces a rapid $Ca^{++}$ fixation at the start then slowly and spreadingly toward the maximum theoretical value of calcium fixation. To the inverse, the concentration of $Na^+$ rapidly diminishes, then more slowly.

The curves of FIGS. 2, 4 and 5 have been established with an aqueous solution of "Manugel GHB" having a concentration of 0.5% the curve of FIG. 4 having been established for a crosslinking solution having a weight concentration of 0.5% expressed in $(CaCl_2.2H_2O)$ and the curves of FIGS. 2 and 5 for a crosslinking solution having a concentration expressed in $(CaCl_2.2H_2O)$ of 0.2% by weight with respect to the weight of the solution.

In these three tests, it has been noted that, when the weight amount of $Ca^{++}$ ions in the capsules is lower than 2.5%, the latter are fragile, soft and their wall is thin; they sink, are deformed and burst too easily. Above a weight amount in $Ca^{++}$ ions of 5.5% the spheres are hard, rubbery, solid, difficult to crush and leave elastic fragments on the skin. The consistency, corresponding to a cosmetic use, lies between the two values. In these tests, the optimum amount of $Ca^{++}$ introduced by bridging in the alginates is close to 4.5% by weight with respect to the dehydrated alginates, this concentration being reached in 1 minute in the case of FIG. 4, in 4 minutes in the case of FIG. 2, and in 1 minute 15 seconds in the case of FIG. 5.

The curve of FIG. 3 corresponds to an aqueous solution of "ALGINIC ACID SODIUM SALT TYPE VI de moyenne viscosite" from Sigma at 0.35% by weight and a crosslinking solution of $(CaCl_2.2H_2O)$ at 0.2 weight percent. The optimum amount of $Ca^{++}$ fixed by bridging, corresponding to alginate capsules having a cosmetic consistency, is from 3.6 to 3.9 weight percent with respect to the weight of the dehydrated alginate and corresponds to a contact time of 1 minute 30 seconds to 2 minutes 15 seconds.

EXAMPLE 2

Alginate capsules are prepared in an apparatus of the type illustrated in FIG. 1 provided with supply nozzles having a diameter of 1.3 mm which deliver droplets at a frequency of 1 Hertz. The contact time between the alginate solution A and the calcium chloride solution B is 2 minutes.

The aqueous alginate solution A has the following composition:

| | |
|---|---|
| Sodium alginate, sold under the trade name "Sigma type VI" | 0.350 g |
| Glycerine | 5.000 g |
| Extract of Gingko Biloba in propylene glycol | 2.000 g |
| Preservative | 0.100 g |
| Demineralized water, sufficient for | 100.000 g |
| Crosslinking solution B has the following composition: | |
| $CaCl_2.2H_2O$ | 0.2 g |
| Surfactant, sold under the commercial name "Tween 20" by ICI Americas | 0.001 g |
| Demineralized water, sufficient for | 100.000 g |

The capsules, removed from solution B, are washed and surface dried. The resulting capsules are spheres having a diameter of 4 mm. They are constituted by a very soft transparent gel, which, after spreading on the skin, accompanied by a light massage, are completely and very rapidly absorbed leaving a sensation of freshness and hydration.

These spheres are then incorporated into a final formulation C, having the following composition:

| | |
|---|---|
| Capsules | 80 g |
| DL alpha-tocopherol | 1 g |
| Cyclic dimethyl polysiloxane, called cyclomethicone in the CTFA Cosmetic Dictionary, 3rd edition, published by the Cosmetic Toiletry and Fragrance Association, sufficient for | 100 g |

After 24 hours it is observed that the capsules have retained their form and individuality in the formulation.

EXAMPLE 3

Alginate capsules are prepared as in Example 1 using an injection nozzle having a diameter of 1.3 mm and a contact time between solutions A and B of 1 minute 15 seconds. Alginate solution A has the following composition:

| | |
|---|---|
| Sodium alginate, sold under the commercial name, "Kelco Manugel GHB" | 0.50 g |
| Glycerine | 4.00 g |
| Aqueous placental Filatov extract | 20.00 g |
| Guanosine crystals | 0.01 g |
| Mica titanium | 0.10 g |
| Preservative, sufficient amount | |
| Demineralized water, sufficient for | 100.000 g |
| Crosslinking solution B has the following composition: | |
| $CaSO_4.5H_2O$ | 0.85 g |
| Surfactant, sold under the trade name "Tween 20" by ICI Americas | 0.001 g |
| Demineralized water, sufficient for | 100.000 g |

The resulting capsules are spheres having a diameter of 4.5 mm. They are incorporated into a final formulation C, having the following composition:

| | |
|---|---|
| Capsules | 95 g |
| Sweet almond oil | 2 g |
| Perfume, sufficient amount | |
| Cyclic dimethyl polysiloxane, called cyclomethicone, in the CTFA Cosmetic Dictionary, 3rd ed., published by the Cosmetic Toiletry and Fragrance Association, sufficient amount for | 100.000 g |

After 24 hours it is noted that the capsules have retained their form and individuality and that they crush easily under the finger.

EXAMPLE 4

Alginate capsules are prepared as in Example 1 using an injection nozzle having a diameter of 0.8 mm and a contact time between the alginate solution A and the calcium salt solution B of 4 minutes.

Solution A has the following composition:

| | |
|---|---|
| Sodium alginate sold under the commercial name "Sigma low viscosity" | 0.50 g |
| Aqueous extract of brown algae | 10 g |
| Aqueous extract of red algae | 10 g |
| Glycerine | 10 g |
| Hydroxyproline | 1 g |
| D-panthenol (vitamin B5) | 1.5 g |
| Preservative, sufficient amount | |
| Demineralized water, sufficient amount for | 100.00 g |
| Solution B has the following composition: | |
| $Zn(CH_3COO)_2.2H_2O$ | 0.3 g |
| Surfactant sold under the commercial name "Tween 20" by ICI Americas | 0.001 g |
| Demineralized water, sufficient amount for | 100.000 g |

The resulting capsules are spheres having a diameter of 2 mm. They are incorporated into an external phase. The final formulation C has the following composition:

| | |
|---|---|
| Capsules | 60 g |
| Polyglycol palmitostearate | 5 g |
| Mineral oil | 3.2 g |
| Preservative, sufficient amount | |
| Perfume, sufficient amount | |
| Demineralized water, sufficient amount for | 100.000 g |

After 24 hours it is noted that the capsules have retained their form and individuality and that they are easily crushed under the finger.

What is claimed is:

1. A cosmetic composition comprising, in a cosmetically acceptable external phase suitable for application to the skin, alginate capsules easily crushed on the skin under the action of a massage without leaving a residue on the skin and having sufficient rigidity so that the structure of said capsules is not modified during storage or on introduction into said cosmetic composition, said alginate capsules being prepared by slowly introducing through at least one nozzle an aqueous solution of at least one alginate into an aqueous solution of at least one polyvalent metal salt, said metal being selected from the group consisting of iron, silver, strontium, aluminum, manganese, selenium, calcium and zinc, removing the resulting alginate capsules, forming by gelification, so as to separate said capsules from the aqueous solution of polyvalent metal and finally, optionally, washing and drying said capsules, wherein at least one alginae has mannuronic units (M) and guluronic units (G) in a M/G molar ratio between 0.4 and 1.9, the amount of blocks (G) being greater than 50 percent, the said alginate being a sodium alginate having a viscosity in a 0.5 weight % aqueous solution lower than 20 mP.s measured with a TV Contraves viscosimeter provided with No. 1 measurement body in the presence of a calcium chelating agent, the weight concentration of said alginate in the aqueous solution introduced through said nozzle being between 0.2 and 2 percent, the molar concentration of the polyvalent metallic cation of the crosslinking aqueous solution of said polyvalent metal salt being between $3.4 \times 10^{-3}$ M and $6.8 \times 10^{-2}$ M, the surface tension of the aqueous solution of polyvalent metal salt being reduced to a value lower than 70 dynes/cm, by the addition of a surface active agent, and the contact time between the drops of alginate solution and the aqueous solution of polyvalent metal salt ranging from 10 seconds to 20 minutes.

* * * * *